United States Patent
Sechrist et al.

(10) Patent No.: US 11,471,786 B2
(45) Date of Patent: Oct. 18, 2022

(54) PROCESS AND SYSTEM FOR PRODUCT RECOVERY AND CELL RECYCLE

(71) Applicant: LanzaTech, Inc., Skokie, IL (US)

(72) Inventors: Paul Alvin Sechrist, Skokie, IL (US); Nicholas Bourdakos, Skokie, IL (US); Robert John Conrado, Skokie, IL (US); Allan Haiming Gao, Skokie, IL (US); Jason Carl Bromley, Skokie, IL (US); Christophe Daniel Mihalcea, Skokie, IL (US); Michael Emerson Martin, Skokie, IL (US); Ignasi Palou-Rivera, Skokie, IL (US); Joseph Henry Tizard, Skokie, IL (US)

(73) Assignee: LanzaTech, Inc., Skokie, IL (US)

( * ) Notice: Subject to any disclaimer, the term of this patent is extended or adjusted under 35 U.S.C. 154(b) by 163 days.

(21) Appl. No.: 16/802,057

(22) Filed: Feb. 26, 2020

(65) Prior Publication Data
US 2020/0188809 A1 Jun. 18, 2020

Related U.S. Application Data

(63) Continuation of application No. 15/926,851, filed on Mar. 20, 2018, now Pat. No. 10,610,802.
(Continued)

(51) Int. Cl.
*B01D 3/10* (2006.01)
*C12M 1/00* (2006.01)
(Continued)

(52) U.S. Cl.
CPC ............. *B01D 3/10* (2013.01); *B01D 3/002* (2013.01); *B01D 19/0057* (2013.01);
(Continued)

(58) Field of Classification Search
CPC ...... B01D 3/002; B01D 3/10; B01D 19/0057; B01D 53/14; C12N 1/02; C12M 47/02; C12M 47/10; C12P 7/04; Y02E 50/30
See application file for complete search history.

(56) References Cited

U.S. PATENT DOCUMENTS 2,176,498 A * 10/1939 Hickman ................. B01D 3/12
261/114.1
4,349,628 A 9/1982 English et al.
(Continued)

OTHER PUBLICATIONS

Office Action issued in corresponding Eurasian Application No. 201991240/31, dated Sep. 18, 2020, 8 pages.
(Continued)

*Primary Examiner* — Gabriel E Gitman
(74) *Attorney, Agent, or Firm* — Frank S. Molinaro

(57) ABSTRACT

The invention is directed to a method for recovering at least one product from a fermentation broth. The invention relates to the use of a vacuum distillation vessel to recover products, such as ethanol, from a fermentation broth, where the fermentation broth comprises viable microbial biomass, and where the recovery of the product is completed in such a manner to ensure the viability of the microbial biomass. The invention provides for product recovery at an effective rate so as to prevent the accumulation of product in the fermentation broth. To ensure the viability of the microbial biomass, the invention is designed to reduce the amount of stress on the microbial biomass. By ensuring the viability of the microbial biomass, the microbial biomass may be recycled and reused in the fermentation process, which may result in an increased efficiency of the fermentation process.

20 Claims, 6 Drawing Sheets

Related U.S. Application Data

(60) Provisional application No. 62/473,850, filed on Mar. 2, 2017.

(51) Int. Cl.
*C12N 1/02* (2006.01)
*B01D 3/00* (2006.01)
*B01D 19/00* (2006.01)
*B01D 53/14* (2006.01)
*C12P 7/04* (2006.01)

(52) U.S. Cl.
CPC ............ *C12M 47/02* (2013.01); *C12M 47/10* (2013.01); *C12N 1/02* (2013.01); *B01D 53/14* (2013.01); *C12P 7/04* (2013.01)

(56) References Cited

U.S. PATENT DOCUMENTS

| | | | | |
|---|---|---|---|---|
| 5,087,737 | A * | 2/1992 | Higuchi | C07C 231/06 560/215 |
| 5,523,509 | A * | 6/1996 | O'Young | B01J 23/34 568/303 |
| 6,136,577 | A * | 10/2000 | Gaddy | C12M 43/02 435/163 |
| 9,150,885 | B2 * | 10/2015 | Shibamoto | C12P 7/04 |
| 2009/0301970 | A1 | 12/2009 | Noel | |
| 2010/0199683 | A1 * | 8/2010 | Mazumder | F02C 6/08 60/785 |
| 2010/0279370 | A1 | 11/2010 | Parten | |
| 2011/0124068 | A1 * | 5/2011 | Evanko | C07C 29/84 426/11 |
| 2012/0211348 | A1 * | 8/2012 | Grady | C07C 29/76 203/42 |
| 2013/0210096 | A1 * | 8/2013 | Schultz | C10G 9/36 435/135 |
| 2014/0238841 | A1 * | 8/2014 | Kawamura | C07C 29/80 203/37 |
| 2015/0152441 | A1 * | 6/2015 | Schultz | B01D 53/0462 435/163 |
| 2015/0152445 | A1 * | 6/2015 | Koepke | C12N 9/1029 435/150 |
| 2015/0232886 | A1 * | 8/2015 | Silverman | C12N 9/16 435/167 |
| 2015/0337343 | A1 * | 11/2015 | Benkwitz | C12P 7/06 435/158 |

OTHER PUBLICATIONS

First Office Action issued in corresponding Chinese Application No. 201880005525.0, dated Apr. 2, 2021, 11 pages.
First Examination Report issued in corresponding Indian Application No. 201917025435, dated Apr. 28, 2021, 5 pages.

* cited by examiner

PROCESS AND SYSTEM FOR PRODUCT RECOVERY AND CELL RECYCLE

CROSS REFERENCE TO A RELATED APPLICATION

The application is a continuation of U.S. application Ser. No. 15/926,851 filed Mar. 20, 2018 which claims the benefit of U.S. Provisional Application No. 62/473,850 filed Mar. 20, 2017, the contents of which are hereby incorporated by reference in their entirety.

FIELD

This invention relates to a device and associated method for recovering at least one product from a fermentation broth. In particular, the invention relates to the use of a vacuum distillation vessel to recover products from a fermentation broth, where the fermentation broth contains viable microbial biomass, and where the recovery of product is completed in such a manner where the viability of the microbial biomass is ensured.

BACKGROUND

Carbon dioxide ($CO_2$) accounts for about 76% of global greenhouse gas emissions from human activities, with methane (16%), nitrous oxide (6%), and fluorinated gases (2%) accounting for the balance (United States Environmental Protection Agency). The majority of $CO_2$ comes from the burning of fossil fuels to produce energy, although industrial and forestry practices also emit $CO_2$ into the atmosphere. Reduction of greenhouse gas emissions, particularly $CO_2$, is critical to halt the progression of global warming and the accompanying shifts in climate and weather.

It has long been recognized that catalytic processes, such as the Fischer-Tropsch process, may be used to convert gases containing carbon dioxide ($CO_2$), carbon monoxide (CO), and/or hydrogen ($H_2$), such as industrial waste gas or syngas, into a variety of fuels and chemicals. Recently, however, gas fermentation has emerged as an alternative platform for the biological fixation of such gases. In particular, C1-fixing microorganisms have been demonstrated to convert gases containing $CO_2$, CO, and/or $H_2$ into products such as ethanol and 2,3-butanediol. The production of such products may be limited, for example, by slow microbial growth, limited gas consumption, sensitivity to toxins, or diversion of carbon substrates into undesired by-products.

The accumulation of products can result in a reduction in the production efficiency of the gas fermentation process. To prevent accumulation, these products must be removed at an effective rate. If not removed at an effective rate, these products may have inhibitory and/or toxic effects on the C1-fixing microorganisms. If the products accumulate to the point that the C1-fixing microorganisms cannot survive, then the fermentation process may have to be stopped and restarted. Prior to being restarted, the fermenters often require cleaning. This can be a time-consuming process.

Another pitfall commonly associated with the recovery of products is the loss of C1-fixing microorganisms through traditional recovery processes. To overcome the loss of viable C1-fixing microorganisms, filtration methods have been employed. However, over time, with traditional filtration methods, particulate matter can build up in the filter media, which can lead to a reduction in the filtrate flux, ultimately requiring cleaning and/or replacement of the filter media.

Accordingly, there remains a need for a system with reduced maintenance requirements that is capable of recovering products at an effective rate while ensuring the viability of the C1-fixing microorganisms.

BRIEF SUMMARY

The invention provides a device, namely, a vacuum distillation vessel, and associated method, that utilizes a vacuum distillation vessel, for recovering at least one product from a fermentation broth. The vacuum distillation vessel is designed for recovering at least one product from a fermentation broth, the fermentation broth being delivered from a bioreactor, the vacuum distillation vessel comprising: (a) an exterior casing, defining an inlet for receiving the fermentation broth, the fermentation broth comprising viable microbial biomass and at least one product, an outlet for transferring a product enriched stream, and an outlet for transferring a product depleted stream, the product depleted stream comprising viable microbial biomass, the product depleted stream being transferred to the bioreactor; and (b) a separation section located within the casing, the separation section being bounded above by an upper tray and below by a lower tray, the separation section defining a separation medium for providing a plurality of theoretical distillation stages; wherein the outlet for transferring the product enriched stream is elevated relative to the inlet for receiving the fermentation broth, the inlet for receiving the fermentation broth being elevated relative to the upper tray, and the outlet for transferring the product depleted stream being elevated relative to the lower tray.

Preferably, the vacuum distillation vessel is capable of processing the fermentation broth at a given feed rate. The feed rate being defined as the volume of fermentation broth per hour. The volume of fermentation broth is the volume of fermentation broth contained in the bioreactor. In at least one embodiment, the vacuum distillation vessel is capable of processing the fermentation broth at a feed rate between 0.05 and 0.5 bioreactor volumes per hour. In certain embodiments, the feed rate is between 0.05 to 0.1, 0.05 to 0.2, 0.05 to 0.3, 0.05 to 0.4, 0.1 to 0.3, 0.1 to 0.1 to 0.5, or 0.3 to 0.5 reactor volumes per hour.

In certain instances, the fermentation broth has a given residence time in the vacuum distillation vessel. The amount of time the fermentation broth is within the vacuum distillation vessel is the amount of time between the moment the fermentation broth enters through the inlet for receiving the fermentation broth, and when the fermentation broth exits through the outlet for transferring the product depleted stream. Preferably, the residence time is between 0.5 and 15 minutes. In various embodiments, the residence time is between 0.5 and 12 minutes, 0.5 and 9 minutes, 0.5 and 6 minutes, 0.5 and 3 minutes, 2 and 15 minutes, 2 and 12 minutes, 2 and 9 minutes, or 2 and 6 minutes. In at least one embodiment, the residence time is less than 15 minutes, less than 12 minutes, less than 9 minutes, less than 6 minutes, less than 3 minutes, less than 2 minutes, or less than 1 minute to ensure the viability of the microorganisms.

The invention provides for the transferring of the product depleted stream to the bioreactor through an outlet in the casing. In at least one embodiment, the casing of the vacuum distillation vessel is connected to the bioreactor by piping means. The product depleted stream may be passed through the piping means from the vacuum distillation vessel to the bioreactor. Preferably, the bioreactor is operated under conditions for fermentation of a C1-containing gas from an industrial process.

The vacuum distillation vessel is designed so as to effectively remove product from the fermentation broth. The vacuum distillation vessel utilizes a separation medium as part of the removal process. The separation medium may be any suitable material to provide adequate vapor-liquid contact.

In certain instances, the separation medium is provided such that the pressure drop over the height of the vacuum distillation vessel is less than 32 mbar. In certain instances, the pressure drop over the height of the vacuum distillation vessel is less than 30 mbar, less than 28 mbar, less than 26 mbar, less than 24 mbar, less than 22 mbar, less than 20 mbar, or less than 18 mbar.

In certain instances, the separation medium is defined by a series of distillation trays. The distillation trays may be any suitable series of distillation trays to provide adequate vapor-liquid contact.

The separation section of the vacuum distillation vessel is designed to provide a plurality of theoretical distillation stages whereby an increasing amount of product is vaporized from the fermentation broth as the fermentation broth passes through the distillation stages. Preferably, the separation medium provides multiple theoretical distillation stages. In certain embodiments, the separation medium provides at least 3 theoretical distillation stages, or at least 5 theoretical stages, or at least 6 theoretical stages.

The vacuum distillation vessel is designed so as to ensure the viability of the microbial biomass. By ensuring the viability of the microbial biomass, the product depleted stream being passed to the bioreactor may be utilized for the gas fermentation process. Preferably, the microbial biomass viability is maintained at a sufficiently high percentage. In certain instances, the viability of the microbial biomass is greater than 80%, or greater than 85%, or greater than 90%, or greater than 95%.

The vacuum distillation vessel may be designed in such a manner that the viability of the microbial biomass is not substantially reduced when passed through the vacuum distillation vessel. In certain instances, the viable microbial biomass in the product depleted stream is substantially equal to the viable microbial biomass in the fermentation broth. Preferably, the difference between the viability of the microbial biomass in the product depleted stream and the viability of the microbial biomass in the fermentation broth is less than 10%. In certain instances, the difference is between 5 and 10%. In certain instances, the difference is less than 5%.

The viability of the microbial biomass may be measured using any suitable means. Preferably, the viability is measured using flow cytometry and a live/dead assay. In certain instances, the measurement of viability of the microbial biomass in the fermentation broth is taken from the fermentation broth before entering the vacuum distillation vessel. In certain instances, the measurement of viability of the microbial biomass in the product depleted stream is taken from the product depleted stream leaving the vacuum distillation vessel before the product depleted stream is passed to the bioreactor.

In certain instances, one or more variable may be changed as a result of the viability measurement. Preferably, the one or more variable changed as a result of the viability measurement is selected from the group comprising: pressure, temperature, residence time, product concentration in fermentation broth, steam feed rate, and separation medium.

Preferably, the product depleted stream has reduced proportions of product relative to the fermentation broth so as to prevent, or at least mitigate, accumulation of product in the fermentation broth. By preventing, or at least mitigating, accumulation of product in the fermentation broth the fermentation process may be continuous. Preferably, product is recovered from a continuous fermentation process. In certain instances, the product depleted stream comprises less than 1 wt. % product, or less than 0.8 wt. % product, or less than 0.6 wt. % product, or less than 0.4 wt. % product or less than 0.2 wt. % product or less than 0.1 wt. % product.

The microorganisms in the bioreactor may be capable of producing a variety of different products. Preferably, one or more products recovered from the continuous fermentation process is a low boiling fermentation product. In certain instances, product is selected from the group consisting of ethanol, acetone, isopropanol, butanol, ketones, methyl ethyl ketone, acetone, 2-butanol, 1-propanol, methyl acetate, ethyl acetate, butanone, 1,3-butadiene, isoprene, and isobutene. In certain instances, the vacuum distillation vessel is designed with specific constraints based upon the product being produced. In certain instances, the product produced in the bioreactor is ethanol, acetone, isopropanol, or mixtures thereof. In various instances, the product enriched stream comprises increased proportions of ethanol, acetone, isopropanol, or mixtures thereof, relative to the fermentation broth. Preferably, the vacuum distillation vessel is designed such that ethanol can be effectively removed from the fermentation broth. In certain instances where ethanol is produced by the microorganisms, the product enriched stream comprises increased proportions of ethanol relative to the fermentation broth. In certain embodiments, the vacuum distillation vessel is designed such that acetone can be effectively removed from the fermentation broth. In certain instances where acetone is produced by the microorganisms, the product enriched stream comprises increased proportions of acetone relative to the fermentation broth. In other embodiments, the vacuum distillation vessel is designed such that isopropanol can be effectively removed from the fermentation broth. In certain instances where isopropanol is produced by the microorganisms, the product enriched stream comprises increased proportions of isopropanol relative to the fermentation broth.

These products may be further converted to produce one or more product. In at least one embodiment, at least one or more product may be further converted to produce at least one component of diesel, jet fuel, and/or gasoline. In certain instances, acetone is further converted to produce methyl methacrylate. In certain instances, isopropanol is further converted to produce propylene.

To effectively remove the product from the fermentation broth, while maintaining microorganism viability, the vacuum distillation vessel operates at a pressure below atmospheric. Preferably, the vacuum distillation vessel is operated at a pressure between 40 mbar(a) and 100 mbar(a), or between 40 mbar(a) and 80 mbar(a), or between 40 mbar(a) and 60 mbar(a), or between 50 mbar(a) and 100 mbar(a), or between 50 mbar(a) and 80 mbar(a), or between 50 mbar(a) and 70 mbar(a), or between 60 mbar(a) and 100 mbar(a), or between 60 mbar(a) and 100 mbar(a), or between 80 mbar(a) and 100 mbar(a).

To effectively remove the product from the fermentation broth, the vacuum distillation operates at a temperature range capable of removing product, while ensuring the viability of the microorganisms. In certain instances, the product is selected from the group consisting of ethanol, acetone, and isopropanol. Preferably, the vacuum distillation vessel is operated at a temperature between 35° C. and 50° C. In one embodiment, the temperature is between 40° C. and 45° C., or between 37° C. and 45° C., or between 45° C. and 50° C. In various instances, the temperature is less than 37° C. In embodiments designed for acetone recovery, the vacuum distillation vessel is preferably operated at a temperature between 35° C. and 50° C. In certain embodiments, for acetone recovery, the temperature is between 35° C. and 45° C., or between 40° C. and 45° C., or between 45° C. and 50° C.

In certain instances, one or more by-products are produced by the fermentation. In certain instances, the one or more by-products are selected from the group consisting of carboxylic acids (i.e. acetic acid and lactic acid) and 2,3-butanediol. In certain instances, the one or more by-products are not separated from the fermentation broth, and are returned to the bioreactor in the product depleted stream. Due to the continuous return of by-products to the bioreactor, the amount of by-product in the fermentation may accumulate. In certain instances, it is desirable to maintain the concentration of by-products in the fermentation broth below a predetermined level. The acceptable concentration of by-products may be determined based on the tolerance of the microbe to the by-product. In certain instances, it may be desirable to provide the product depleted stream to a secondary separation means to remove one or more by-product from the product depleted stream. In certain embodiments the by-product is 2,3-butanediol and the concentration of 2,3-butaendiol in the fermentation broth is maintained below 10 g/L. In certain instances, the by-product is acetic acid and the concentration of acetic acid in the fermentation broth is maintained below 10 g/L In certain instances, the temperature of the product depleted stream is elevated such that the product depleted stream needs to be cooled prior to being passed to the bioreactor. The temperature of the stream may have a direct effect on the viability of the microorganism. For instance, higher temperatures may result in a decrease in microorganism viability. To avoid the negative effects of increased temperature, the product depleted stream may be cooled by any suitable cooling means prior to being sent to the bioreactor. Preferably, the temperature of the product depleted stream is cooled to between 35° C. and 40° C. prior to being returned to the bioreactor. Preferably, the fermentation broth and the product depleted stream are kept below 45° C. to avoid the detrimental effects on viability. In one embodiment, the temperature is between 37° C. and 45° C. to avoid detrimental effects. In certain instances, the temperature is dependent on the microorganism being used. The effect of temperature on microorganism viability may be heightened at higher residence times. For instance, at higher residence times, when the temperature is above optimal, viability of the microorganisms may decrease.

In certain instances, the fermentation broth may contain proportions of gas. Gas in the fermentation broth has been shown to negatively impact the performance of the vacuum distillation vessel. This decrease in performance may be due, at least in part, on the correlation between gas in the fermentation broth and production of foam in the vacuum distillation vessel. To reduce the proportions of gas in the fermentation broth, a degassing vessel may be utilized. When utilizing a degassing vessel, the inlet for receiving the fermentation broth may be connected by piping means to the degassing vessel. The degassing vessel is operated under conditions to remove at least a portion of the gas from the fermentation broth prior to the fermentation broth being delivered to the vacuum distillation vessel.

In certain instances, the degassing vessel is operated at pressure. In certain instances, the degassing vessel is operated at any pressure less than the operating pressure of the bioreactor. Preferably, the degassing vessel is operated at a pressure between 0.0 bar (g) and 1.0 bar (g). In one embodiment, the degassing vessel is operated at a pressure between 0.0 bar (g) and 0.5 bar (g). Preferably, the degassing vessel removes substantially all of the gas from the fermentation broth. In particular embodiments, the degassing vessel removes between 0 and 100% of the gas in the fermentation broth. In certain instances, the degassing vessel removes more than 20%, more than 40%, more than 60%, or more than 80% of the gas from the fermentation broth. In certain instances, the degassing vessel removes at least a portion of carbon dioxide from the fermentation broth. In certain instances, the degassing vessel removes at least 20%, or at least 40%, or at least 60%, or at least 80% of carbon dioxide from the fermentation broth.

The vacuum distillation vessel may receive a vapor stream from a reboiler. If designed to receive a vapor stream from a reboiler, the exterior casing of the vacuum distillation vessel may further define an inlet for receiving the vapor stream. This vapor stream may be produced from liquid from the vacuum distillation vessel. When utilizing liquid from the vacuum distillation vessel, the liquid may be transferred via an outlet in the casing of the vacuum distillation vessel. To effectively transfer the vapor stream to the vacuum distillation vessel, the inlet for receiving the vapor stream may be located subjacent relative to the lower tray, and the outlet for transferring the liquid stream may be located lower relative to the inlet for receiving the vapor stream.

Preferably, the liquid stream is comprised substantially of water and minimal amounts of microbial biomass. The vacuum distillation vessel is designed to transfer viable microbial biomass back to the bioreactor. The viable microbial biomass is contained in the product depleted stream. The vacuum distillation vessel transfers the product depleted to the bioreactor through the outlet for transferring the product depleted stream. The outlet for transferring the product depleted stream is placed above the lower tray. Fermentation broth, containing microbial biomass, may pass through this lower tray. This fermentation broth passing through may then mix with the liquid in the bottom of the vacuum distillation vessel. Preferably, only minimal amounts of microbial biomass end up in the liquid in the bottom of the vacuum distillation vessel. Preferably, less than 0.042 reactor volumes of the fermentation broth, containing the microbial biomass, pass through the lower tray per hour. In certain instances, between 0.002 and 0.042 reactor volumes of the fermentation broth, containing the microbial biomass, pass through the lower tray per hour. In various embodiments, less than 0.042, less than 0.037, less than 0.032, less than 0.027, less than 0.022, less than 0.017, less than 0.012, less than 0.007, reactor volumes of the fermentation broth, containing the microbial biomass, pass through the lower tray per hour. This liquid, including components of fermentation broth containing microbial biomass, is then passed to the reboiler to produce the vapor stream.

The vacuum distillation vessel may incorporate one or more additional trays below the lower tray. The one or more additional trays may provide for additional product removal. When including one or more additional trays, the fermentation broth that passes through the lower tray is passed to the one or more additional trays where additional amounts of product may be recovered. After passing through the one or more additional trays, the fermentation broth mixes with the liquid in the bottom of the vacuum distillation vessel. This liquid, including components of fermentation broth containing microbial biomass, is then passed to the reboiler to produce the vapor stream.

The vacuum distillation vessel may be separated into multiple compartments. Preferably, when the vacuum distillation vessel is separated into multiple compartments, the fermentation broth within each compartment is contained such that the fermentation broth from one compartment does not mix with fermentation broth from another compartment. This separation may be achieved through any suitable means. In certain instances, the fermentation broth may be sourced from multiple bioreactors. The product depleted stream from the fermentation broth may be sent back to the bioreactor from which the fermentation broth was derived. By preventing mixing between the multiple compartments, one vacuum distillation vessel may be utilized to effectively recover product from a plurality of bioreactors.

Preferably, the bioreactor that provides the fermentation broth is utilized for fermentation of a C1-containing substrate. This C1-containing substrate utilized in the fermentation process may be sourced from one or more industrial processes. Preferably, the industrial process is selected from the group comprising: carbohydrate fermentation, gas fermentation, cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs and catalytic processes (derived from the steam sources including but not limited to steam methane reforming, steam naphtha reforming, petroleum coke gasification, catalyst regeneration—fluid catalyst cracking, catalyst regeneration-naphtha reforming, and dry methane reforming).

The invention provides for a method for removing at least one product from the fermentation broth by utilizing a vacuum distillation vessel, the method comprising: (a) passing a fermentation broth comprising viable microbial biomass and at least one product from a bioreactor to a vacuum distillation vessel; (b) partially vaporizing the fermentation broth to produce a product enriched stream and a product depleted stream, the product depleted stream comprising viable microbial biomass; and (c) passing the product depleted stream back to the bioreactor. The invention may be designed in such a manner that the viability of the microbial biomass in the fermentation broth is ensured such that, when passed to the bioreactor, the microbial biomass will be utilized for fermentation of a C1-containing substrate.

Preferably, the gas in the fermentation broth is monitored and controlled. Gas in the fermentation broth may result in a decrease in performance of the vacuum distillation vessel. To control the gas in the fermentation broth a degassing step may be necessary. If the fermentation broth contains higher than acceptable proportions of gas, fermentation broth is passed to a degassing means prior to passing a degassed fermentation broth to the vacuum distillation vessel.

The degassing step may be completed such that an evolved gas stream is separated from the fermentation broth, producing a degassed fermentation broth. The degassed fermentation broth is then able to be partially vaporized by the vacuum distillation vessel, producing the product enriched stream and the product depleted stream.

The portion of gas that forms the evolved gas stream may contain proportions of product. To prevent product loss through removal of gas, the evolved gas stream may be sent to the subsequent processing. In certain instances, the evolved gas stream is passed to a water scrubber to recover at least one product. In certain instances, the evolved gas stream may be sent to the bioreactor.

The method may utilize a vacuum distillation vessel that comprises a separation section located within a casing. Preferably, the separation section located within the casing is bounded above by an upper tray and below by a lower tray. The separation section may provide multiple theoretical distillation stages.

The fermentation broth being processed may contain any suitable microorganism. For example, the microorganism may be selected from the group comprising: *Escherichia coli, Saccharomyces cerevisiae, Clostridium acetobutylicum, Clostridium beijerinckii, Clostridium saccharbutyricum, Clostridium saccharoperbutylacetonicum, Clostridium butyricum, Clostridium diolis, Clostridium kluyveri, Clostridium pasterianium, Clostridium novyi, Clostridium difficile, Clostridium thermocellum, Clostridium cellulolyticum, Clostridium cellulovorans, Clostridium phytofermentans, Lactococcus lactis, Bacillus subtilis, Bacillus licheniformis, Zymomonas mobilis, Klebsiella oxytoca, Klebsiella pneumonia, Corynebacterium glutamicum, Trichoderma reesei, Cupriavidus necator, Pseudomonas putida, Lactobacillus plantarum,* and *Methylobacterium extorquens*. In certain instances, the microorganism may be a C1-fixing bacterium selected from the group comprising: *Acetobacterium woodii, Alkalibaculum bacchii, Blautia producta, Butyribacterium methylotrophicum, Clostridium aceticum, Clostridium autoethanogenum, Clostridium carboxidivorans, Clostridium coskatii, Clostridium drakei, Clostridium formicoaceticum, Clostridium ljungdahlii, Clostridium magnum, Clostridium ragsdalei, Clostridium scatologenes, Eubacterium limosum, Moorella thermautotrophica, Moorella thermoacetica, Oxobacter pfennigii, Sporomusa ovata, Sporomusa silvacetica, Sporomusa sphaeroides,* and *Thermoanaerobacter kiuvi*. Preferably, the microorganism is a member of the genus *Clostridium*. In certain instances, the microorganism is *Clostridium autoethanogenum*.

The microorganisms may be capable of producing a variety of different products. Preferably, one or more products produced by the microorganisms is a low boiling fermentation product. In certain instances, product is selected from the group consisting of ethanol, acetone, isopropanol, butanol, ketones, methyl ethyl ketone, acetone, 2-butanol, 1-propanol, methyl acetate, ethyl acetate, butanone, 1,3-butadiene, isoprene, and isobutene. In certain instances, the method is optimized based upon the product being produced. In certain instances, the product produced in the bioreactor is ethanol. Preferably, the method is optimized such that ethanol can be effectively removed from the fermentation broth. In certain instances, the microorganism produces at least one by-product. In one embodiment the at least one by-product is selected from the group consisting of acetic acid, lactic acid and 2,3-butanediol.

DETAILED DESCRIPTION

Figure 1:
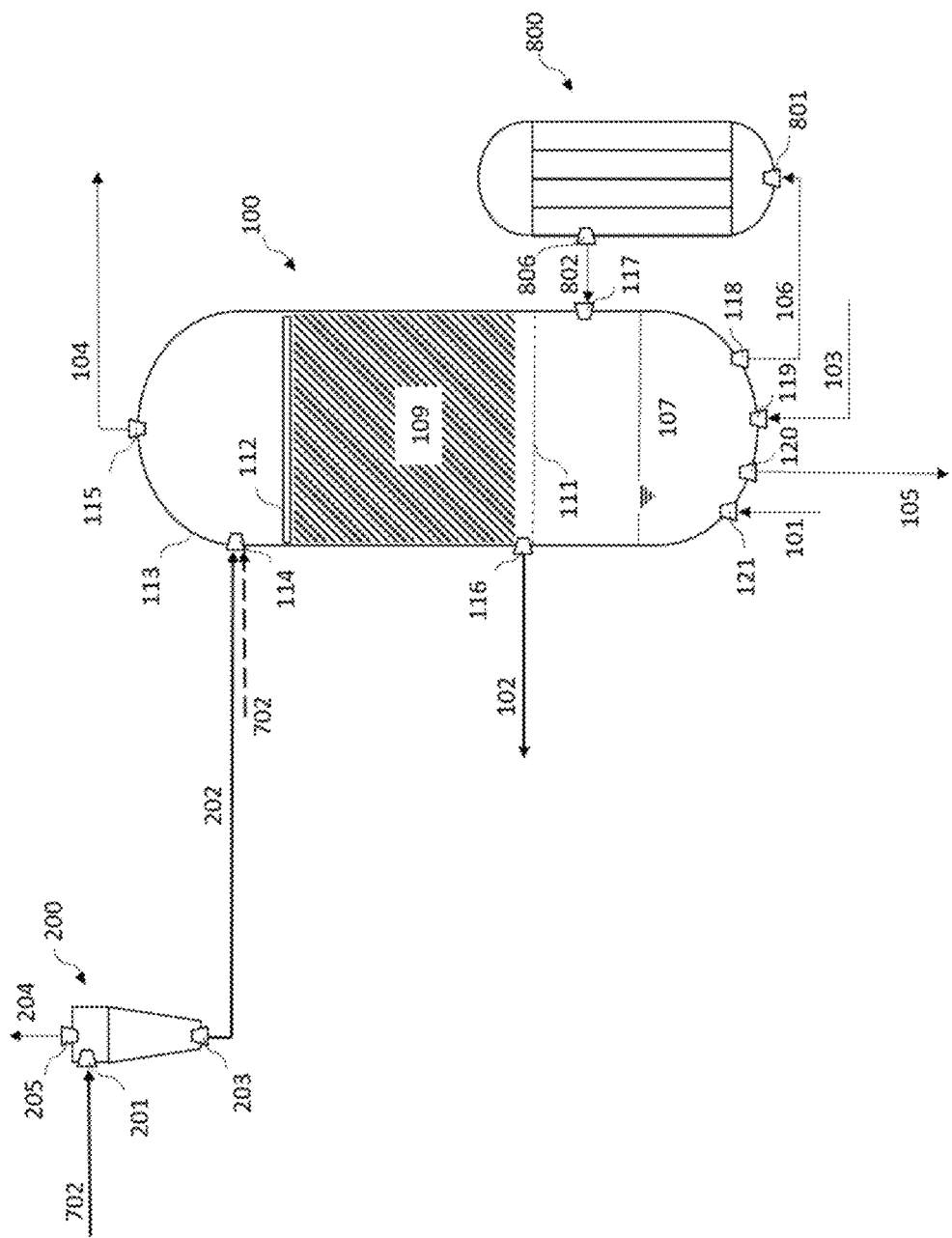
FIG. 1 is a schematic flow diagram showing the vacuum distillation vessel, degassing vessel, and reboiler, in accordance with one aspect of the invention.

The inventors have identified that by using a particularly designed vacuum distillation vessel, at least one product, such as ethanol, may be effectively recovered from a fermentation broth, containing viable microbial biomass, while ensuring the viability of the microbial biomass.

Definitions

The term "vacuum distillation vessel" is intended to encompass a device for conducting distillation under vacuum, wherein the liquid being distilled is enclosed at a low pressure to reduce its boiling point. Preferably, the vacuum distillation vessel includes a casing for enclosing a separation medium. Preferably, the liquid being distilled is fermentation broth comprising viable microbial biomass and at least one product. Such fermentation broth may be sourced from a bioreactor. The bioreactor may be used for fermentation of a C1-containing substrate.

"Casing" refers to the cover or shell protecting or enclosing the separation medium. Preferably, the casing includes a number of inlets and outlets for transferring liquid and/or gas. The casing should include at least one inlet for receiving fermentation broth, at least one outlet for transferring a product enriched stream, and at least one outlet for transferring a product depleted stream.

"Separation medium" is used to describe any suitable medium capable of providing a large surface area for vapor-liquid contact, which increases the effectiveness of the vacuum distillation column. Such separation medium is designed to provide a plurality of theoretical distillation stages. In at least one embodiment, the separation medium is a series of distillation trays.

"Distillation trays" or "distillation plates" and the like are intended to encompass plates and/or trays used to encourage vapor-liquid contact. Tray types include sieve, valve, and bubble cap. Sieve trays which contain holes for vapor to flow through are used for high capacity situations providing high efficiency at a low cost. Although less expensive, valve trays, containing holes with opening and closing valves, have the tendency to experience fouling due to the accumulation of material. Bubble cap trays contain caps and are the most advanced and expensive of the three trays, and are highly effective in some liquid flow rate situations.

Preferably, the "upper tray" is any suitable boundary whereby the fermentation broth may be distributed downward to the separation medium.

Preferably, the "lower tray" is any suitable boundary to effectuate the transfer of the product depleted stream through the outlet in the casing.

A "theoretical distillation stage" is a hypothetical zone in which two phases, such as the liquid and vapor phases of a substance, establish an equilibrium with each other. The performance of many separation processes depends on having a series of theoretical distillation stages. The performance of a separation device, such as a vacuum distillation vessel, may be enhanced by providing an increased number of stages. Preferably, the separation medium includes a sufficient number of theoretical distillation stages to effectively remove at least one product from the fermentation broth. Preferably, the separation medium includes multiple theoretical distillation stages.

The term "fermentation broth" or "broth" is intended to encompass the mixture of components including the nutrient media, the culture of one or more microorganisms, and the one or more products. It should be noted that the term microorganism and the term bacteria are used interchangeably throughout the document.

"Nutrient media" or "nutrient medium" is used to describe bacterial growth media. Generally, this term refers to a media containing nutrients and other components appropriate for the growth of a microbial culture. The term "nutrient" includes any substance that may be utilised in a metabolic pathway of a microorganism. Exemplary nutrients include potassium, B vitamins, trace metals and amino acids.

Preferably, the fermentation broth is sent from a "bioreactor" to the vacuum distillation vessel. The term "bioreactor" includes a fermentation device consisting of one or more vessels and/or towers or piping arrangements, which includes the Continuous Stirred Tank Reactor (CSTR), Immobilized Cell Recycles (ICR), Trickle Bed Reactor (TBR), Bubble Column, Gas Lift Fermenter, Static Mixer, a circulated loop reactor, a membrane reactor, such as a Hollow Fibre Membrane Bioreactor (HFM BR) or other vessel or other device suitable for gas-liquid contact. The reactor is preferably adapted to receive a gaseous substrate comprising CO or $CO_2$ or $H_2$ or mixtures thereof. The reactor may comprise multiple reactors (stages), either in parallel or in series. For example, the reactor may comprise a first growth reactor in which the bacteria are cultured and a second fermentation reactor, to which fermentation broth from the growth reactor may be fed and in which most of the fermentation products may be produced.

"Gaseous substrates comprising carbon monoxide" include any gas which contains carbon monoxide. The gaseous substrate will typically contain a significant proportion of CO, preferably at least about 5% to about 100% CO by volume.

While it is not necessary for the substrate to contain any hydrogen, the presence of H2 should not be detrimental to product formation in accordance with methods of the invention. In particular embodiments, the presence of hydrogen results in an improved overall efficiency of alcohol production. For example, in particular embodiments, the substrate may comprise an approx. 2:1, or 1:1, or 1:2 ratio of $H_2$:CO. In one embodiment, the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment, the substrate comprises less than or equal to about 20% $CO_2$ by volume. In particular embodiments, the substrate comprises less than or equal to about 15% $CO_2$ by volume, less than or equal to about 10% $CO_2$ by volume, less than or equal to about 5% $CO_2$ by volume or substantially no $CO_2$.

The use of a vacuum distillation vessel with a bioreactor may increase the efficiency of the fermentation process. The terms "increasing the efficiency", "increased efficiency" and the like, when used in relation to a fermentation process, include, but are not limited to, increasing one or more of the rate of growth of microorganisms catalysing the fermentation, the growth and/or product production rate at elevated product concentrations, the volume of desired product produced per volume of substrate consumed, the rate of production or level of production of the desired product, and the relative proportion of the desired product produced compared with other by-products of the fermentation.

Unless the context requires otherwise, the phrases "fermenting", "fermentation process" or "fermentation reaction" and the like, as used herein, are intended to encompass both the growth phase and product biosynthesis phase of the microorganisms.

The fermentation process may be described as either "batch" or "continuous". "Batch fermentation" is used to describe a fermentation process where the bioreactor is filled with raw material, i.e. the carbon source, along with microorganisms, where the products remain in the bioreactor until fermentation is completed. In a "batch" process, after fermentation is completed, the products are extracted and the bioreactor is cleaned before the next "batch" is started. "Continuous fermentation" is used to describe a fermentation process where the fermentation process is extended for longer periods of time, and product and/or metabolite is extracted during fermentation. Preferably, the vacuum distillation vessel removes product from a "continuous fermentation" process.

A "microorganism" is a microscopic organism, especially a bacterium, archea, virus, or fungus. The microorganism of the invention is typically a bacterium. As used herein, recitation of "microorganism" should be taken to encompass "bacterium."

"Viability" or "viability of the microbial biomass" and the like refers to the ratio of microorganisms that are alive, capable of living, developing, or reproducing to those that are not. For example, viable microbial biomass in a vacuum distillation vessel may refer to the ratio of live/dead microorganisms within the vacuum distillation vessel. The invention may be designed so that the viability of the microbial biomass is maintained at a minimum viability. In at least one embodiment, the viability of the microbial biomass is at least about 85%. In at least one embodiment, the viable microbial biomass is returned from the vacuum distillation vessel back to the bioreactor.

"Effective rate of product recovery" and the like refers to the rate at which product can be recovered from the fermentation broth so as to prevent, or at least mitigate, the toxic and/or inhibitory effects associated with product accumulation. The invention may be designed so that the effective rate of product recovery is such that the viability of the microbial biomass is maintained above a desired threshold. The invention may be designed so that the level of product concentration in the broth is kept below a desired threshold. For example, the invention may be designed such that the ethanol concentration in the fermentation broth is kept below 40 g/L. In certain instances, the ethanol concentration in the fermentation broth is kept between 25 to 35 g/L. In particular instances, the ethanol concentration in the fermentation broth is less than 30 g/L, less than 3 5g/L, or less than 38 g/L. Preferably, the ethanol concentration in the fermentation broth is less than the concentration that may result in inhibition of the microorganism. In particular instances, the inhibition may be dependent on the microorganism being used and the product being produced.

The vacuum distillation vessel may pass the product depleted stream to a "cooling means" prior to the product depleted stream being passed to the bioreactor. The term "cooling means" may describe any suitable device or process capable of reducing the temperature of the product depleted stream.

The microorganisms in bioreactor may be modified from a naturally-occurring microorganism. A "parental microorganism" is a microorganism used to generate a microorganism of the invention. The parental microorganism may be a naturally-occurring microorganism (i.e., a wild-type microorganism) or a microorganism that has been previously modified (i.e., a mutant or recombinant microorganism). The microorganism of the invention may be modified to express or overexpress one or more enzymes that were not expressed or overexpressed in the parental microorganism. Similarly, the microorganism of the invention may be modified to contain one or more genes that were not contained by the parental microorganism. The microorganism of the invention may also be modified to not express or to express lower amounts of one or more enzymes that were expressed in the parental microorganism. In one embodiment, the parental microorganism is *Clostridium autoethanogenum*, *Clostridium ljungdahlii*, or *Clostridium ragsdalei*. In a preferred embodiment, the parental microorganism is *Clostridium autoethanogenum* LZ1561, which was deposited on Jun. 7, 2010 with Deutsche Sammlung von Mikroorganismen and Zellkulturen GmbH (DSMZ) located at InhoffenstraB 7B, D-38124 Braunschwieg, Germany on Jun. 7, 2010 under the terms of the Budapest Treaty and accorded accession number DSM23693. This strain is described in International Patent Application No. PCT/NZ2011/000144, which published as WO 2012/015317.

"Wood-Ljungdahl" refers to the Wood-Ljungdahl pathway of carbon fixation as described, i.e., by Ragsdale, *Biochim Biophys Acta*, 1784: 1873-1898, 2008. "Wood-Ljungdahl microorganisms" refers, predictably, to microorganisms containing the Wood-Ljungdahl pathway. Generally, the microorganism of the invention contains a native Wood-Ljungdahl pathway. Herein, a Wood-Ljungdahl pathway may be a native, unmodified Wood-Ljungdahl pathway or it may be a Wood-Ljungdahl pathway with some degree of genetic modification (i.e., overexpression, heterologous expression, knockout, etc.) so long as it still functions to convert CO, $CO_2$, and/or $H_2$ to acetyl-CoA.

"C1" refers to a one-carbon molecule, for example, CO, $CO_2$, $CH_4$, or $CH_3OH$. "C1-oxygenate" refers to a one-carbon molecule that also comprises at least one oxygen atom, for example, CO, $CO_2$, or $CH_3OH$. "C1-carbon source" refers a one carbon-molecule that serves as a partial or sole carbon source for the microorganism of the invention. For example, a C1-carbon source may comprise one or more of CO, $CO_2$, $CH_4$, $CH_3OH$, or $CH_2O_2$. Preferably, the C1-carbon source comprises one or both of CO and $CO_2$. A "C1-fixing microorganism" is a microorganism that has the ability to produce one or more products from a C1-carbon source. Typically, the microorganism of the invention is a C1-fixing bacterium.

An "anaerobe" is a microorganism that does not require oxygen for growth. An anaerobe may react negatively or even die if oxygen is present above a certain threshold. However, some anaerobes are capable of tolerating low levels of oxygen (i.e., 0.000001-5% oxygen). Typically, the microorganism of the invention is an anaerobe.

"Acetogens" are obligately anaerobic bacteria that use the Wood-Ljungdahl pathway as their main mechanism for energy conservation and for synthesis of acetyl-CoA and acetyl-CoA-derived products, such as acetate (Ragsdale, *Biochim Biophys Acta*, 1784: 1873-1898, 2008). In particular, acetogens use the Wood-Ljungdahl pathway as a (1) mechanism for the reductive synthesis of acetyl-CoA from $CO_2$, (2) terminal electron-accepting, energy conserving process, (3) mechanism for the fixation (assimilation) of $CO_2$ in the synthesis of cell carbon (Drake, Acetogenic Prokaryotes, In: The Prokaryotes, $3^{rd}$ edition, p. 354, New York, N.Y., 2006). All naturally occurring acetogens are C1-fixing, anaerobic, autotrophic, and non-methanotrophic. Typically, the microorganism of the invention is an acetogen.

An "ethanologen" is a microorganism that produces or is capable of producing ethanol. Typically, the microorganism of the invention is an ethanologen.

An "autotroph" is a microorganism capable of growing in the absence of organic carbon. Instead, autotrophs use inorganic carbon sources, such as CO and/or $CO_2$. Typically, the microorganism of the invention is an autotroph.

A "carboxydotroph" is a microorganism capable of utilizing CO as a sole source of carbon and energy. Typically, the microorganism of the invention is a carboxydotroph.

A "methanotroph" is a microorganism capable of utilizing methane as a sole source of carbon and energy. In certain embodiments, the microorganism of the invention is a methanotroph or is derived from a methanotroph. In other embodiments, the microorganism of the invention is not a methanotroph or is not derived from a methanotroph.

"Substrate" refers to a carbon and/or energy source for the microorganism of the invention. Typically, the substrate is gaseous and comprises a C1-carbon source, for example, CO, $CO_2$, and/or $CH_4$. Preferably, the substrate comprises a C1-carbon source of CO or CO+$CO_2$. The substrate may further comprise other non-carbon components, such as $H_2$, $N_2$, or electrons.

The term "co-substrate" refers to a substance that, while not necessarily being the primary energy and material source for product synthesis, can be utilised for product synthesis when added to another substrate, such as the primary substrate.

Although the substrate is typically gaseous, the substrate may also be provided in alternative forms. For example, the substrate may be dissolved in a liquid saturated with a CO-containing containing gas using a microbubble dispersion generator. By way of further example, the substrate may be adsorbed onto a solid support.

The substrate and/or C1-carbon source may be a waste gas obtained as a by-product of an industrial process or from some other source, such as from automobile exhaust fumes or biomass gasification. In certain embodiments, the industrial process is selected from the group consisting gas emissions from carbohydrate fermentation, gas fermentation, gas emissions from cement making, pulp and paper making, steel making, oil refining and associated processes, petrochemical production, coke production, anaerobic or aerobic digestion, synthesis gas (derived from sources including but not limited to biomass, liquid waste streams, solid waste streams, municipal streams, fossil resources including natural gas, coal and oil), natural gas extraction, oil extraction, metallurgical processes, for production and/or refinement of aluminium, copper, and/or ferroalloys, geological reservoirs, and catalytic processes (derived from the steam sources including but not limited to steam methane reforming, steam naphtha reforming, petroleum coke gasification, catalyst regeneration—fluid catalyst cracking, catalyst regeneration-naphtha reforming, and dry methane reforming). In these embodiments, the substrate and/or C1-carbon source may be captured from the industrial process before it is emitted into the atmosphere, using any convenient method.

The microorganism of the invention may be cultured with the gas stream to produce one or more products. For instance, the microorganism of the invention may produce or may be engineered to produce ethanol (WO 2007/117157), acetate (WO 2007/117157), butanol (WO 2008/115080 and WO 2012/053905), butyrate (WO 2008/115080), 2,3-butanediol (WO 2009/151342 and WO 2016/094334), lactate (WO 2011/112103), butene (WO 2012/024522), butadiene (WO 2012/024522), methyl ethyl ketone (2-butanone) (WO 2012/024522 and WO 2013/185123), ethylene (WO 2012/026833), acetone (WO 2012/115527), isopropanol (WO 2012/115527), lipids (WO 2013/036147), 3-hydroxypropionate (3-HP) (WO 2013/180581), terpenes, including isoprene (WO 2013/180584), fatty acids (WO 2013/191567), 2-butanol (WO 2013/185123), 1,2-propanediol (WO 2014/036152), 1-propanol (WO 2014/0369152), chorismate-derived products (WO 2016/191625), 3-hydroxybutyrate (WO 2017/066498), and 1,3-butanediol (WO 2017/0066498).

A "native product" is a product produced by a genetically unmodified microorganism. For example, ethanol, acetate, and 2,3-butanediol are native products of *Clostridium autoethanogenum*, *Clostridium ljungdahlii*, and *Clostridium ragsdalei*. A "non-native product" is a product that is produced by a genetically modified microorganism, but is not produced by a genetically unmodified microorganism from which the genetically modified microorganism is derived.

"Selectivity" refers to the ratio of the production of a target product to the production of all fermentation products produced by a microorganism. The microorganism of the invention may be engineered to produce products at a certain selectivity or at a minimum selectivity. In one embodiment, a target product accounts for at least about 5%, 10%, 15%, 20%, 30%, 50%, 75%, or 95% of all fermentation products produced by the microorganism of the invention. In one embodiment, the target product accounts for at least 10% of all fermentation products produced by the microorganism of the invention, such that the microorganism of the invention has a selectivity for the target product of at least 10%. In another embodiment, the target product accounts for at least 30% of all fermentation products produced by the microorganism of the invention, such that the microorganism of the invention has a selectivity for the target product of at least 30%.

The vacuum distillation vessel is capable of recovering one or more "low boiling fermentation product." A "low boiling fermentation product" is a product that is volatile. These products may include, but are not limited to, ethanol, acetone, isopropanol, butanol, ketones, methyl ethyl ketone, 2-butanol, 1-propanol, methyl acetate, ethyl acetate, butanone, 1,3-butadiene, isoprene, and isobutene.

The culture is generally maintained in an aqueous culture medium that contains nutrients, vitamins, and/or minerals sufficient to permit growth of the microorganism. Preferably the aqueous culture medium is an anaerobic microbial growth medium, such as a minimal anaerobic microbial growth medium. Suitable media are well known in the art.

The culture/fermentation should desirably be carried out under appropriate conditions for production of the target product. Typically, the culture/fermentation is performed under anaerobic conditions. Reaction conditions to consider include pressure (or partial pressure), temperature, gas flow rate, liquid flow rate, media pH, media redox potential, agitation rate (if using a continuous stirred tank reactor), inoculum level, maximum gas substrate concentrations to ensure that gas in the liquid phase does not become limiting, and maximum product concentrations to avoid product inhibition. In particular, the rate of introduction of the substrate may be controlled to ensure that the concentration of gas in the liquid phase does not become limiting, since products may be consumed by the culture under gas-limited conditions.

Operating a bioreactor at elevated pressures allows for an increased rate of gas mass transfer from the gas phase to the liquid phase. Accordingly, it is generally preferable to perform the culture/fermentation at pressures higher than atmospheric pressure. Also, since a given gas conversion rate is, in part, a function of the substrate retention time and retention time dictates the required volume of a bioreactor, the use of pressurized systems can greatly reduce the volume of the bioreactor required and, consequently, the capital cost of the culture/fermentation equipment. This, in turn, means that the retention time, defined as the liquid volume in the bioreactor divided by the input gas flow rate, can be reduced when bioreactors are maintained at elevated pressure rather than atmospheric pressure. The optimum reaction conditions will depend partly on the particular microorganism used. However, in general, it is preferable to operate the fermentation at a pressure higher than atmospheric pressure. Also, since a given gas conversion rate is in part a function of substrate retention time and achieving a desired retention time in turn dictates the required volume of a bioreactor, the use of pressurized systems can greatly reduce the volume of the bioreactor required, and consequently, the capital cost of the fermentation equipment.

Description

Vacuum distillation has been found to effectively recover product from fermentation broth while ensuring the viability of the microorganisms contained in the fermentation broth. The fermentation broth being fed to the vacuum distillation vessel is sourced from a bioreactor. Preferably, the bioreactor is used for fermentation of a C1-containing gaseous substrate. In order for the fermentation process to operate continuously, at least a portion of the microorganisms contained in the broth must remain viable. These microorganisms have fairly specific tolerances to concentrations of certain products. Additionally, these microorganisms have fairly specific tolerances to temperature. For example, in at least one embodiment, the microorganisms have an optimum growth temperature of 37° C. The inventors have found that by utilizing vacuum distillation, the conditions for viability are able to be controlled in such a manner that continuous operation of the fermentation process is possible.

The vacuum distillation vessel consists of multiple elements: (1) an exterior casing defining at least one inlet for receiving fermentation broth, one outlet for transferring a product enriched stream, and one outlet for transferring a product depleted stream; (2) a separation section located within the casing, the separation section being bounded above by an upper tray and below by a lower tray, the separation section defining a separation medium for providing a plurality of theoretical distillation stages; and (3) a liquid level maintained at the bottom of the vacuum distillation vessel.

The vacuum distillation vessel is coupled with the bioreactor so as to effectively process the fermentation broth. It was found by the inventors that by feeding the vacuum distillation vessel at a given feed rate, product accumulation in the bioreactor is controlled, thereby ensuring the viability of the microorganisms. Feed rate is given in terms of volumes of fermentation broth of the bioreactor per hour. The inventors have identified that a feed rate between 0.05 and 0.5 reactor volumes per hour allows for the broth to be effectively processed, while ensuring the viability of the microorganisms. The feed rate may be dependent, at least in part, on the vacuum distillation vessel conditions, including but not limited to, pressure, temperature, residence time, product concentration in fermentation broth, steam feed rate, and/or separation medium. In certain embodiments, the feed rate is between 0.05 to 0.1, 0.05 to 0.2, 0.05 to 0.3, 0.05 to 0.4, 0.1 to 0.3, 0.1 to 0.1 to 0.5, or 0.3 to 0.5 reactor volumes per hour. Preferably, the feed rate is controlled such that the product depleted stream has acceptable proportions of product.

Additionally, the inventors have identified that by keeping the residence time, being defined as the time that the fermentation broth is within the vacuum distillation vessel, within a certain period of time, the viability of the microorganisms is ensured. The inventors have identified that a residence time between 0.5 and 15 minutes allows for the broth to be effectively processed, while ensuring the viability of the microorganisms. In various embodiments, the residence time is between 0.5 and 12 minutes, 0.5 and 9 minutes, 0.5 and 6 minutes, 0.5 and 3 minutes, 2 and 15 minutes, 2 and 12 minutes, 2 and 9 minutes, or 2 and 6 minutes. In at least one embodiment, the residence time is less than 15 minutes, less than 12 minutes, less than 9 minutes, less than 6 minutes, less than 3 minutes, less than 2 minutes, or less than 1 minute to ensure the viability of the microorganisms.

The vacuum distillation vessel processes the fermentation broth through use of pressure reduction, where the pressure inside the vacuum distillation vessel is maintained below atmospheric so as to lower the temperature necessary to vaporize the liquid in the fermentation broth. The temperature in the vacuum distillation vessel may be dependent on the pressure and ethanol concentration. Preferably, the liquid being vaporized is primarily product, such as ethanol. Preferably, the pressure of the vacuum distillation vessel is maintained between 40 mbar(a) and 100 mbar(a) to ensure the viability of the microorganisms. In at least one embodiment, the vacuum distillation vessel is maintained between 40 mbar(a) and 80 mbar(a), between 40 mbar(a) and 90 mbar(a), or between 45 mbar(a) to 90 mbar(a). The pressure typically drops over the separation medium, meaning that the pressure at the top of the vacuum distillation vessel is lower relative to the pressure at the bottom of the vacuum distillation vessel. Preferably, the pressure drop over the height of the vacuum distillation vessel is less than 32 mbar. In certain instances, the pressure drop over the height of the vacuum distillation vessel is less than 30 mbar, less than 28 mbar, less than 26 mbar, less than 24 mbar, less than 22 mbar, less than 20 mbar, or less than 18 mbar.

This results in a temperature gradient within the vacuum distillation vessel where the temperature increases over the length of the vessel, being lowest at the top of the vacuum distillation vessel and highest at the bottom of the vacuum distillation vessel. As the fermentation broth flows down the vacuum distillation vessel the product titer is reduced, where the product titer is highest at the top of the vacuum distillation vessel and lowest at the bottom of the vacuum distillation vessel.

The fermentation broth initially enters the vacuum distillation vessel via an inlet in the casing. The inlet for receiving the fermentation broth is located above the upper tray. As the fermentation broth enters the vessel, a portion of the product in the fermentation broth is vaporized forming a product enriched stream, which rises toward the top of the vessel, exiting through an outlet in the casing. The outlet for transferring the product enriched stream is elevated relative to the inlet for receiving the fermentation broth. The remaining fermentation broth passes through the upper tray and through the separation medium. The separation medium provides a plurality of theoretical distillation stages. As the fermentation broth reaches each theoretical distillation stage additional product is vaporized. The vaporized product becoming part of the product enriched stream, rising toward the top of the vessel, and exiting through an outlet in the casing. After passing through the separation medium, the remaining fermentation broth exits the vacuum distillation vessel via an outlet in the casing. The fermentation broth exiting the casing is the product depleted stream. The product depleted stream contains viable microbial biomass. The outlet for transferring the product depleted stream is elevated relative to the lower tray. The lower tray is elevated relative to the bottom of the vacuum distillation vessel. The bottom of the vacuum distillation vessel contains a level of liquid.

In order to increase the effectiveness of the vacuum distillation vessel and provide for the necessary vapor-liquid contact, a vapor stream may be introduced from a reboiler to the vacuum distillation vessel via an inlet in the casing. The inlet for receiving the vapor stream is located subjacent to the lower tray. The reboiler utilizes a portion of the liquid from the bottom of the vacuum distillation vessel in combination with energy to vaporize the liquid and create the vapor stream. The liquid from the bottom of the vacuum distillation vessel is transferred via an outlet in the vacuum distillation vessel casing. This outlet is located lower than the inlet for receiving the vapor stream. The vapor stream flows upward through the separation medium, picks up portions of product, and becomes part of the product enriched stream. The product enriched stream exiting through the outlet for transferring the product enriched stream. In one or more embodiment, the product enriched stream may be further processed in order to increase the concentration of the product.

The fermentation broth being passed to the vacuum distillation vessel may contain proportions of gas. Gas in the fermentation broth may result in a decrease in performance of the vacuum distillation vessel. To prevent the performance decrease associated with gas in the fermentation broth, a degassing vessel may be utilized. Preferably, the degassing vessel is a cyclonic degasser. Preferably, the degassing vessel is operated at a pressure between 0.0 bar (g) and 1.0 bar (g). In one embodiment, the degassing vessel is operated at a pressure between 0.0 bar (g) and 0.5 bar (g). Preferably, the degassing vessel removes substantially all of the gas from the fermentation broth. In particular embodiments, the degassing vessel removes between 0 and 100% of the gas in the fermentation broth. In certain instances, the degassing vessel removes more than 20%, more than 40%, more than 60%, or more than 80% of the gas from the fermentation broth. The degassing vessel is operated so as to separate at least a portion of the gas from the fermentation broth. When utilizing a cyclonic degasser, the fermentation broth is rotated, creating a low-pressure region at the center of the rotating fermentation broth, causing the gas to separate from the fermentation broth. The fermentation broth with reduced proportions of gas is then sent to the vacuum distillation vessel. The separated gas may contain proportions of product. To recover product from the separated gas and avoid loss of product, the separated gas may be sent to a subsequent device and/or processing. In at least one embodiment, the separated gas may be passed to the bioreactor.

Preferably, the product depleted stream leaving the vacuum distillation vessel is passed back to the bioreactor. The product depleted stream contains viable microbial biomass, which, if passed back to the bioreactor, will increase the efficiency of the fermentation process. However, this product depleted stream may have a higher than optimal temperature. Therefore, prior to being passed back to the bioreactor, the product depleted stream may undergo cooling. The cooling of the product depleted stream may be completed by way of a cooling means. The cooling is conducted under conditions to reduce the temperature of the product depleted stream such that the product depleted stream temperature is within an optimal range. By reducing the temperature of the product depleted stream prior to passing the product depleted stream to the bioreactor, unnecessary heating of the culture in the bioreactor can be avoided. For example, if the product depleted stream were to be provided to the bioreactor at a higher temperature relative to the fermentation broth within the bioreactor, then the recycling of the product depleted stream could result in a temperature increase of the fermentation broth within the bioreactor. If the temperature of the fermentation broth within the bioreactor is not maintained within an acceptable range, suitable for the microorganisms, then the viability of the microorganisms could decrease. Thus, monitoring and controlling the temperature of the product depleted stream may be critical to the ability of recycling the product depleted stream.

FIG. 1 shows a vacuum distillation vessel 100 for recovering at least one product from a fermentation broth, the fermentation broth being delivered from a bioreactor. The vacuum distillation vessel 100 comprises an exterior casing 113, defining an inlet 114 for receiving fermentation broth, an outlet 115 for transferring a product enriched stream via piping 104, and an outlet 116 for transferring a product depleted stream. The vacuum distillation vessel 100 also comprises a separation section 109 located within the casing 113, the separation section 109 is bounded above by an upper tray 112 and below by a lower tray 111. The vacuum distillation vessel 100 is designed in a way to increase the recovery of product from the fermentation broth. The outlet 115 for transferring the product enriched stream is elevated relative to the inlet 114 for receiving the fermentation broth. The inlet 114 for receiving the fermentation broth being elevated relative to the upper tray 112, the outlet 116 for transferring the product depleted stream being elevated relative to the lower tray 111.

The vacuum distillation vessel 100 is designed such that the vacuum distillation vessel 100 can process fermentation broth at a given feed rate. The feed rate is defined in terms of volume of fermentation broth in the bioreactor. Preferably, the vacuum distillation vessel 100 is designed such that the feed rate is between 0.05 to 0.5.

The vacuum distillation vessel 100 is designed such that the fermentation broth defines a residence time. The residence time is defined in terms of the amount of time the fermentation broth is within the vacuum distillation vessel 100. The fermentation broth is deemed to be within the vacuum distillation vessel 100 when the fermentation broth enters through the inlet 114. The fermentation broth is deemed to be out of the vacuum distillation vessel 100 when the fermentation broth exits through the outlet 116. Preferably, the residence time is between 0.5 and 15 minutes. In various embodiments, the residence time is between 0.5 and 12 minutes, 0.5 and 9 minutes, 0.5 and 6 minutes, 0.5 and 3 minutes, 2 and 15 minutes, 2 and 12 minutes, 2 and 9 minutes, or 2 and 6 minutes. In at least one embodiment, the residence time is less than 15 minutes, less than 12 minutes, less than 9 minutes, less than 6 minutes, less than 3 minutes, less than 2 minutes, or less than 1 minute to ensure the viability of the microorganisms.

The given residence time may depend, at least in part, on the type of separation medium 109 within the vacuum distillation vessel 100. In at least one embodiment, the separation medium 109 is defined by a series of distillation trays. Preferably, a separation medium 109 is provided such that a sufficient number of theoretical distillation stages are provided to recover product. Preferably, the separation medium 109 provides multiple theoretical distillation stages. In other embodiments, the separation medium 109 provides a minimum number of theoretical distillation stages, for example, more than 3 theoretical distillation stages, more than 4 theoretical distillation stages, more than 5 theoretical distillation stages, or more than 6 theoretical distillation stages.

The vacuum distillation vessel 100 is designed so as to effectively recover product in the fermentation broth and prevent product accumulation in the bioreactor. Preferably, the product depleted stream has reduced proportions of product such that product accumulation is effectively reduced or eliminated. In at least one embodiment, the product depleted stream comprises less than 0.2 wt. % product. In certain embodiments, the product depleted stream comprises less than 1.0 wt. % product. In particular instances, the product depleted stream comprises between 0.1 and 1.0 wt. % product. In at least one embodiment, the product being recovered is ethanol.

To effectuate the transfer of the product depleted stream, the outlet 116 for transferring the product depleted stream may be connected via piping means 102 to the bioreactor. The product depleted stream may have higher than acceptable temperature, and thus may require cooling prior to being transferred to the bioreactor. To effectuate cooling, a cooling means may be provided. The cooling means may bring the product depleted stream to an acceptable temperature prior to the product depleted stream being transferred to the bioreactor.

In some instances, the fermentation broth may have higher than acceptable proportions of gas, and thus may require degassing prior to being transferred to the bioreactor. To effectuate degassing, a degassing vessel 200 may be provided. Preferably, the degassing vessel 200 is a cyclonic degasser. The degassing vessel 200 may comprise an inlet 201 for receiving the fermentation broth. This inlet 201 may be connected via piping means 702 to the bioreactor in order to transfer the fermentation broth from the bioreactor. Preferably, the degassing vessel 200 is operated such that at least a portion of gas can be removed from the fermentation broth prior to the fermentation broth being delivered to the vacuum distillation vessel 100. The degassing vessel 200 is capable of separating the gas from the fermentation broth such the fermentation broth is separated into an evolved gas stream and a degassed fermentation broth. The evolved gas stream exits the degassing vessel 200 via the outlet 205. The outlet 205 may be connected via piping means 204 to a subsequent process to recover product from the evolved stream. In at least one embodiment, the evolved gas stream is water scrubbed to recover product in the evolved gas stream. Additionally, the outlet 205 may be connected to the bioreactor via piping means 204 where the evolved gas may be used in the fermentation process. The degassed fermentation broth is passed through an outlet 203 to the vacuum distillation vessel 100 via piping means 202. In at least one embodiment, the degassing vessel 200 is operated at a pressure between 0.0 bar(g) and 0.5 bar(g). In embodiments not utilizing a degassing vessel 200, the fermentation broth may be sent directly from the bioreactor to the inlet 114 in the vacuum distillation vessel 100 via piping means 702.

The vacuum distillation vessel 100 is designed so as to ensure the viability of the microorganisms while providing product recovery. Preferably, the viability of the microorganisms in the product depleted stream is greater than 85 percent. In at least one embodiment, the viability of the microorganisms in the product depleted stream is substantially equal to the viable microbial biomass in the incoming fermentation broth.

The vacuum distillation vessel 100 may provide for product recovery through use of a reboiler 800. The reboiler 800 is provided so as to direct a vapor stream to the vacuum distillation vessel 100. This vapor stream is directed through piping means 802 from the outlet 806 in the reboiler to the inlet 117 in the casing 113 of the vacuum distillation vessel 100. The vapor stream enters the vacuum distillation vessel 100 and rises upward through the lower plate 111 and the separation medium 109 contacting the product in the fermentation broth. The reboiler 800 may create the vapor stream through use of liquid 107 located in the bottom of the vacuum distillation vessel 100. Preferably, this liquid 107 is comprised substantially of water and minimal amounts of microbial biomass. The liquid 107 may be passed through piping means 106 from an outlet 118 in the vacuum distillation vessel 100 to an inlet 801 in the reboiler 800. In various embodiments, the liquid 107 located in the bottom of the vacuum distillation vessel 100 may be derived from a number of sources including, but not limited to, the cooling means, steam condensate, a cogeneration unit, and/or the rectification column bottoms.

The casing 113 of the vacuum distillation vessel 100 may comprise one or more additional inlets 121, 119 and outlet 120 for transferring liquid 107 via piping 101, 103, and 105 into and out of the vacuum distillation vessel 100. This may allow for the content and proportion of the liquid 107 in the vacuum distillation vessel 100 to be controlled. In certain instances, the piping 101, 103, and 105 may be connected to one or more of the sources of the liquid 107.

Additionally, the vacuum distillation vessel 100 may be designed such that the vacuum distillation vessel 100 is separated into multiple compartments in a manner where fermentation broth from multiple bioreactors may be passed to the vacuum distillation vessel 100 without mixing. This separation may be achieved through any means suitable to ensure such separation.

Figure 2:
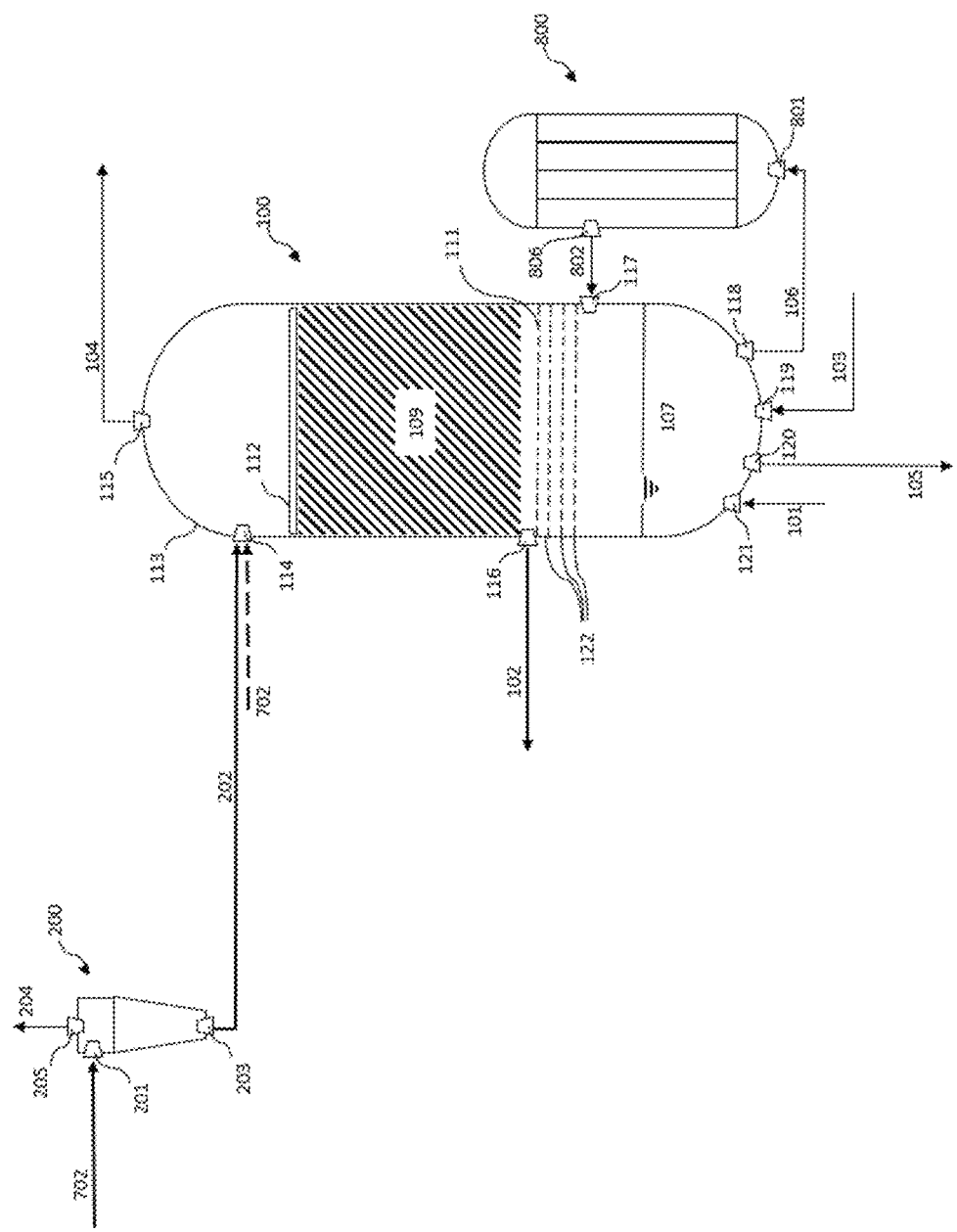
FIG. 2 is a schematic flow diagram showing the vacuum distillation vessel, degassing vessel, and reboiler, where the vacuum distillation vessel includes one or more additional trays below the lower tray, in accordance with one aspect of the invention.

The vacuum distillation vessel may contain one or more additional tray 122 below the lower tray 111. FIG. 2 illustrates a vacuum distillation vessel 100 with additional trays 122 below the lower tray 111. These additional trays 122 provide for additional product removal. The vacuum distillation vessel 100 is designed to transfer fermentation broth, containing the viable microbial biomass, to the bioreactor through the outlet 116, which is placed above the lower tray 111. The fermentation broth that passes through the lower tray 111 may contain additional, albeit minimal, amounts of fermentation broth containing the viable microbial biomass. The fermentation broth that passes through the lower tray 111 is not passed to the bioreactor. This fermentation broth is instead passed through the one or more additional trays 122 where additional product is recovered from the fermentation broth. After passing through the one or more additional trays 122, the fermentation broth mixes with the liquid 107 located in the bottom of the vacuum distillation vessel 100. This liquid 107, including portions of fermentation broth containing microbial biomass, is then passed to the reboiler 800 to produce the vapor stream.

Figure 3:
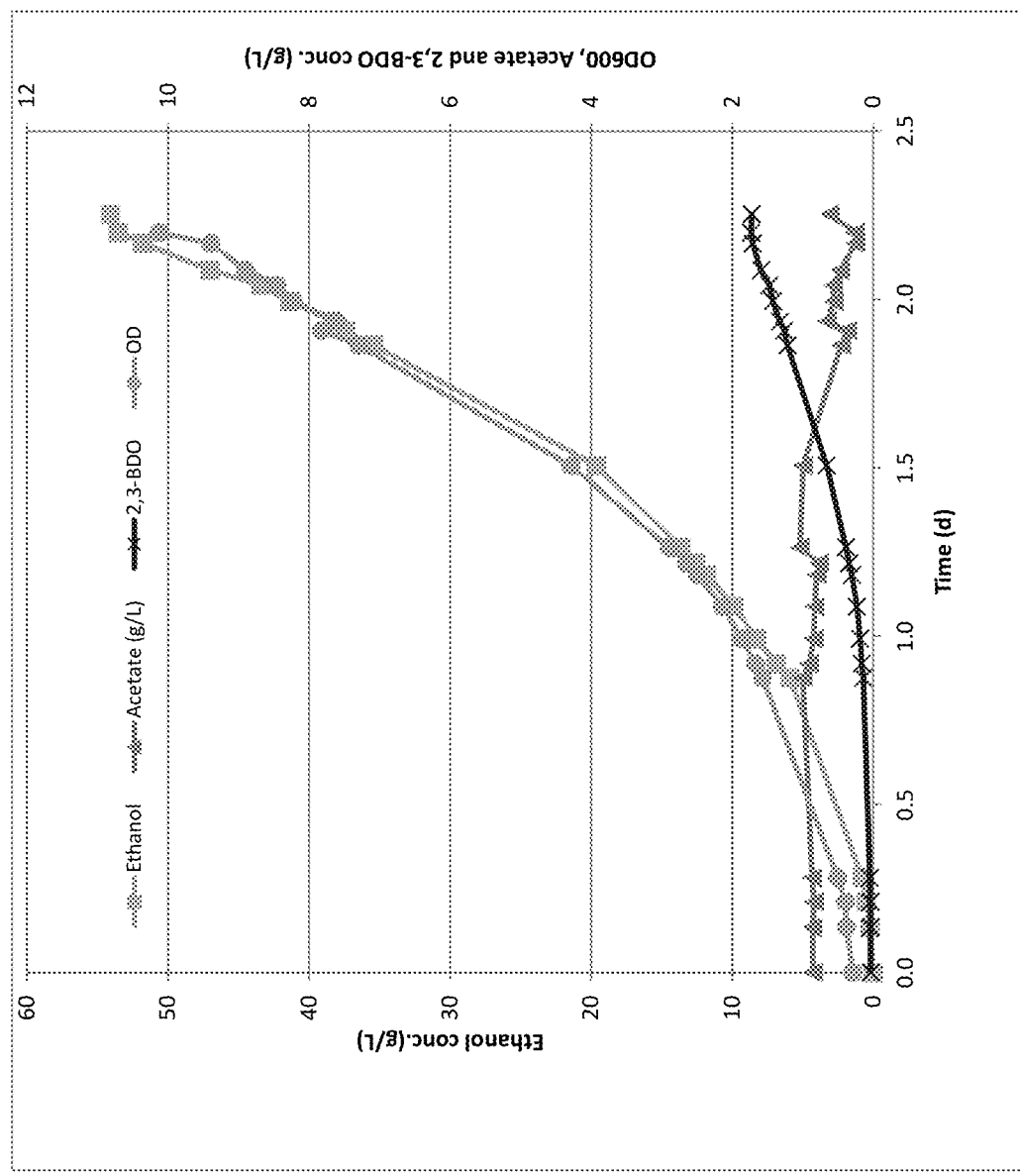
FIG. 3 is a graph showing the metabolite profile of a batch fermentation run, in accordance with one aspect of the invention.
Figure 4:
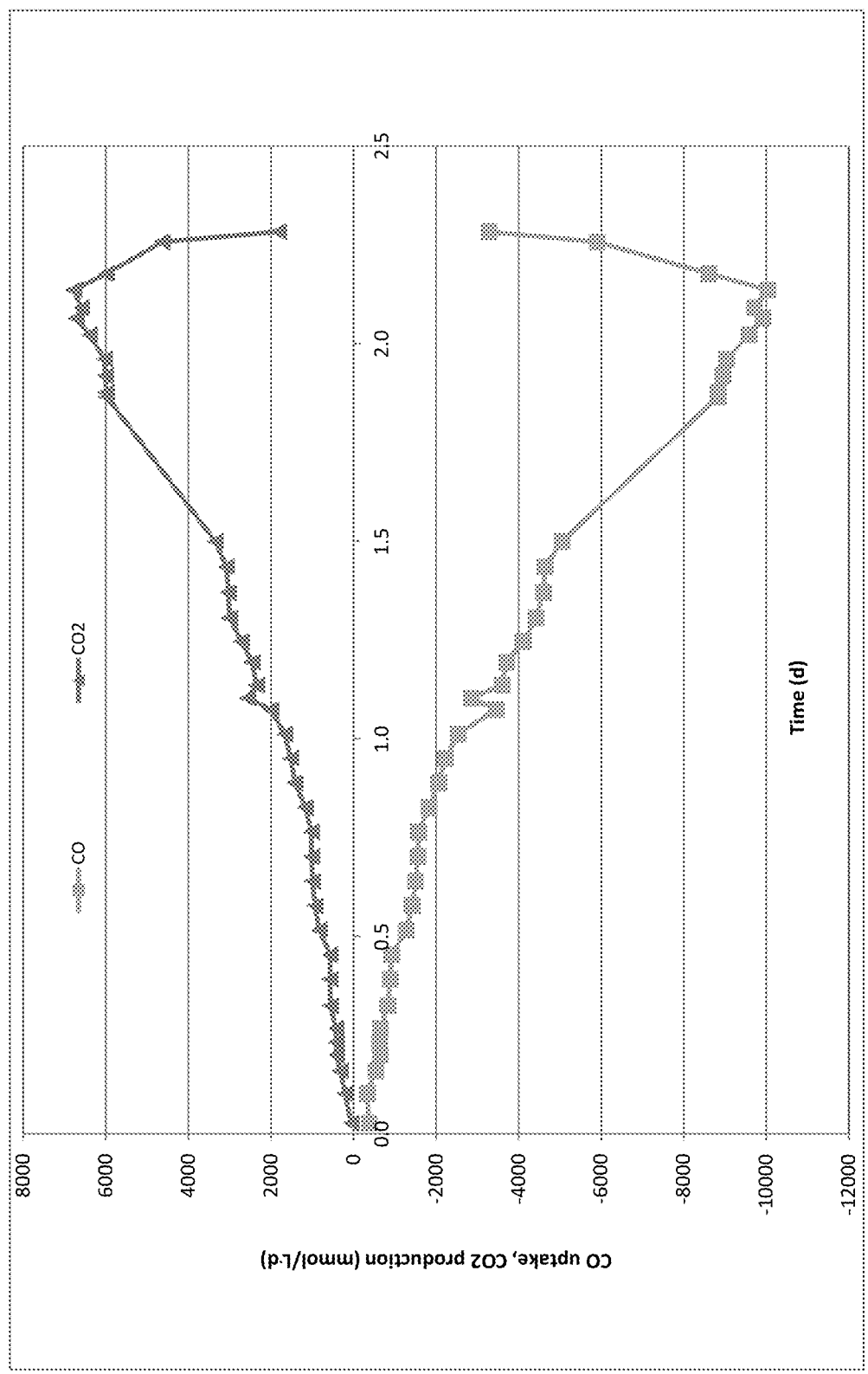
FIG. 4 is a graph showing the gas uptake of the batch fermentation run corresponding with the metabolite profile shown in FIG. 3, in accordance with one aspect of the invention.

FIGS. 3 and 4 illustrate the need for a vacuum distillation vessel to remove product from the fermentation broth. FIG. 3 shows the metabolite profile of a batch fermentation run.

FIG. 3 shows that the biomass and ethanol concentration increases exponentially during the initial phase of the fermentation run. As the ethanol accumulates, exceeding a concentration around 30 g/L, the biomass slows down due to the effects of the ethanol on the microbes. This is further shown by FIG. 4, where the CO uptake and $CO_2$ production slows down around the same time that the ethanol concentration reaches around 30 g/L. This data illustrates the needs for the vacuum distillation vessel of the current invention, where product concentration rates can be controlled to the point where the negative effects of product accumulation are mitigated and/or reduced.

Figure 5:
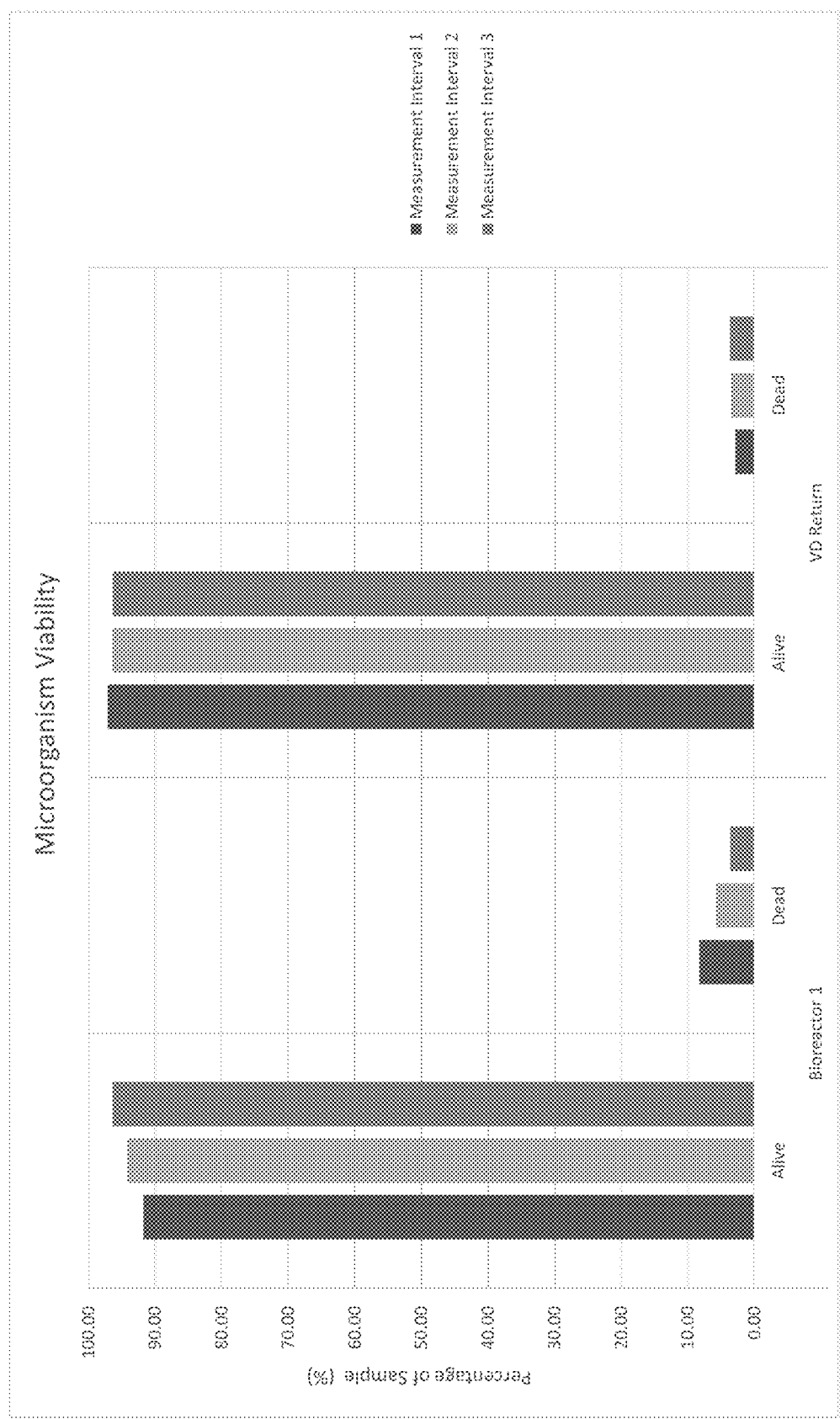
FIG. 5 is a graph showing the viability of the microorganisms passing through the vacuum distillation vessel from a bioreactor with a certain configuration, in accordance with one aspect of the invention.
Figure 6:
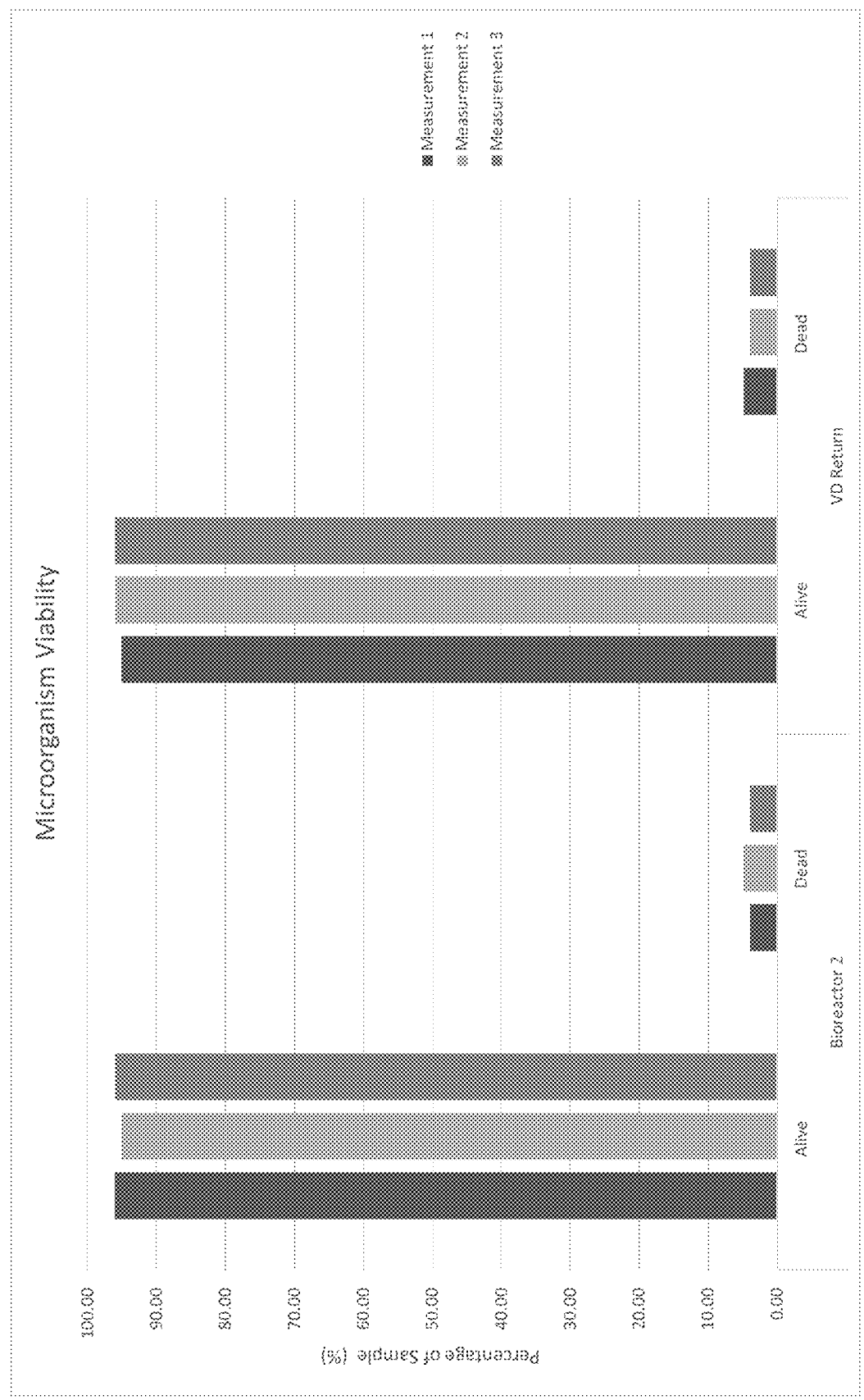
FIG. 6 is a graph showing the viability of the microorganisms passing through the vacuum distillation vessel from a bioreactor with a different configuration than that shown in FIG. 5, in accordance with one aspect of the invention.

The vacuum distillation vessel is capable of recycling product depleted fermentation broth to the bioreactor. The vacuum distillation vessel is designed to recover products, while ensuring the viability of the microorganisms so that, when recycled, the microorganisms may ferment the C1-containing gas in the bioreactor to produce products. FIGS. 5 and 6 illustrate the ability of the vacuum distillation vessel to ensure the viability of the microorganisms from multiple variations of bioreactor designs.

FIG. 5 shows the viability of microorganisms from a bioreactor with a certain configuration, where the fermentation broth is recycled from the vacuum distillation vessel to the bioreactor. The viability of the microorganisms was measured at three times intervals from the bioreactor (Bioreactor 1) and from the vacuum distillation vessel (VD return). As is shown in the graph, the viability of the microorganisms in the vacuum distillation vessel is substantially equal to the viability of the microorganisms in the bioreactor.

FIG. 6 shows the viability of the microorganisms from a bioreactor with a different configuration, where the fermentation broth is recycled from the vacuum distillation vessel to the bioreactor. The viability of the microorganisms was measured at three times intervals from the bioreactor (Bioreactor 2) and from the vacuum distillation vessel (VD return). As shown in the graph, the viability of the microorganisms in the vacuum distillation vessel is substantially equal to the viability of the microorganisms in the bioreactor.

All references, including publications, patent applications, and patents, cited herein are hereby incorporated by reference to the same extent as if each reference were individually and specifically indicated to be incorporated by reference and were set forth in its entirety herein. The reference to any prior art in this specification is not, and should not be taken as, an acknowledgement that that prior art forms part of the common general knowledge in the field of endeavour in any country.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for producing and recovering at least one product from a fermentation process comprising:
    a. introducing a C1-containing gas substrate from a source to a bioreactor containing at least one microorganism capable of fermenting the C1-containing gas substrate and producing at least one product and at least one by-product;
    b. generating a fermentation broth in the bioreactor comprising the at least one microorganism as viable microbial biomass, the at least one product, and the at least one by-product;
    c. passing the fermentation broth from the bioreactor to a vacuum distillation vessel;
    d. partially vaporizing the fermentation broth to produce a product enriched stream and a product depleted stream, the product depleted stream comprising the viable microbial biomass and the at least one by-product; and
    e. passing the product depleted stream to a secondary separation unit to remove the at least one by-product before passing the product depleted stream back to the bioreactor, wherein the fermentation broth has a residence time in the vacuum distillation vessel from about 0.5 to about 15 minutes and wherein the difference between the viability of the microbial mass in the product depleted stream and the viability of the microbial biomass in the fermentation broth is less than 10%.

2. The method of claim 1, further comprising passing the product enriched stream to a conversion unit to convert the at least one product into a secondary product.

3. The method of claim 2, wherein the secondary product is at least one component of diesel fuel, jet fuel, and/or gasoline.

4. The method of claim 2, wherein the at least one product is acetone and the secondary product is methyl methacrylate.

5. The method of claim 2, wherein the at least one product is isopropanol and the secondary product is propylene.

6. The method of claim 1, wherein the source is selected from a carbohydrate fermentation process, a gas fermentation process, a cement making process, a pulp and paper making process, a steel making process, an oil refining process, a petrochemical production process, a coke production process, an anaerobic digestion process, an aerobic digestion process, a synthesis gas production process, a natural gas extraction process, an oil extraction process, a metallurgical process, a geological reservoir and a catalytic process.

7. The method of claim 6, wherein the synthesis gas production process utilizes a feedstock selected from biomass, a liquid waste stream, a solid waste stream, a municipal stream, a fossil resource, and combinations thereof.

8. The method of claim 7, wherein the fossil resource is selected from natural gas, coal, oil, and combinations thereof.

9. The method of claim 6, wherein the metallurgical process is selected from the production and/or refinement of aluminum, the production and/or refinement of copper, the production and/or refinement of ferroalloys and combinations thereof.

10. The method of claim 6, wherein the catalytic process is selected from steam methane reforming, steam naphtha reforming, petroleum coke gasification, catalyst regeneration in fluid catalyst cracking, catalyst regeneration in naphtha reforming, dry methane reforming, and combinations thereof.

11. The method of claim 1, wherein the at least one by-product is a carboxylic acid and/or 2,3-butanediol.

12. The method of claim 1, further comprising degassing the fermentation broth to produce a degassed fermentation broth and an evolved gas stream, prior to passing the fermentation broth to the vacuum distillation vessel.

13. A method for producing and recovering at least one product from a fermentation process comprising:
   a. introducing a C1-containing gas substrate from a source to a bioreactor containing at least one microorganism capable of fermenting the C1-containing gas substrate;
   b. generating a fermentation broth in the bioreactor comprising the at least one microorganism as viable microbial biomass, and at least one fermentation product;
   c. passing the fermentation broth from the bioreactor to a vacuum distillation vessel;
   d. partially vaporizing the fermentation broth to produce a fermentation product enriched stream and a fermentation product depleted stream, the fermentation product depleted stream comprising the viable microbial biomass, wherein the fermentation broth has a residence time in the vacuum distillation vessel from about 0.5 to about 15 minutes and wherein the difference between the viability of the microbial mass in the fermentation product depleted stream and the viability of the microbial biomass in the fermentation broth is less than 10%;
   e. passing the fermentation product depleted stream back to the bioreactor; and
   f. introducing the fermentation product enriched stream to a conversion unit to convert the at least one fermentation product into a secondary product.

14. The method of claim 13, wherein the secondary product is at least one component of diesel fuel, jet fuel, and/or gasoline.

15. The method of claim 13, wherein the at least one fermentation product is acetone, and the secondary product is methyl methacrylate.

16. The method of claim 13, wherein the at least one fermentation product is isopropanol, and the secondary product is propylene.

17. The method of claim 13, further comprising degassing the fermentation broth to produce a degassed fermentation broth and an evolved gas stream prior to passing the fermentation broth to the vacuum distillation vessel.

18. The method of claim 17, wherein the evolved gas stream is water-scrubbed to recover at least one product.

19. The method of claim 13, wherein the vacuum distillation vessel comprises a separation section located within a casing, the separation section being bound above by an upper tray and below by a lower tray, the separation section defining a separation medium for providing a plurality of theoretical distillation stages.

20. The method of claim 13, wherein the bioreactor is operated under conditions for fermentation of a C1-containing gas from an industrial process.

* * * * *